United States Patent [19]

Parodi

[11] Patent Number: 5,954,764
[45] Date of Patent: Sep. 21, 1999

[54] DEVICE FOR CONCURRENTLY PLACING AN ENDOVASCULAR EXPANDER WITH AN ENDOVASCULAR PROSTHESIS

[76] Inventor: Juan Carlos Parodi, Blanco Encalada 1543/47 1 piso, Ciudad de Buenos Aires, Argentina

[21] Appl. No.: 08/931,992

[22] Filed: Sep. 17, 1997

[30] Foreign Application Priority Data

Sep. 20, 1996 [AR] Argentina .................................. 338,240

[51] Int. Cl.⁶ .................................................. A61F 2/06
[52] U.S. Cl. ........................................................ 623/1
[58] Field of Search ........................................ 623/1, 12

[56] References Cited

U.S. PATENT DOCUMENTS

| | | | |
|---|---|---|---|
| 5,693,083 | 12/1997 | Baker | 623/1 |
| 5,709,703 | 1/1998 | Lukic | 623/1 |
| 5,723,003 | 3/1998 | Winston | 623/1 |
| 5,733,267 | 3/1998 | Del Toro | 623/1 |
| 5,746,766 | 5/1998 | Edoga | 623/1 |
| 5,749,848 | 5/1998 | Jang | 623/1 |

*Primary Examiner*—Michael J. Milano
*Attorney, Agent, or Firm*—Ratner & Prestia

[57] ABSTRACT

A device for endoluminally placing an endovascular tubular prosthesis in a vascular duct along a guide wire. The device comprises an introducer exterior sheath and an interior sheath therein, with the prosthesis positioned between the sheaths and an elastic expander compressed inside the interior sheath. The expander furthest end exteriorly projects from the interior sheath and is joined to the tubular prosthesis furthest end. A pusher is linked to the expander nearest end, and may contain a radiopaque substance where it connects to the expander. The expander may have an expanded length that is longer than the length of the prosthesis.

6 Claims, 3 Drawing Sheets

DEVICE FOR CONCURRENTLY PLACING AN ENDOVASCULAR EXPANDER WITH AN ENDOVASCULAR PROSTHESIS

FIELD OF THE INVENTION

The present invention relates generally to a delivery system for delivering and deploying a medical device, and more specifically, to a device for placing an endovascular prosthesis into a vascular duct concurrently with placement of an endovascular expander, or stent.

BACKGROUND OF THE INVENTION

As an alternative to traditional surgical vascular treatments where tissues are cut to reach a damaged artery or vein, "endovascular" treatments are now frequently used. Endovascular treatments are carried out at the lumen of the vessel. Some exemplary purposes and means for such treatments may be:

a) to produce artery or vein dilatation,
 b) to dissolve thrombus in their interior,
 c) to close abnormal communications of vessels among each other or with neighboring tissues,
 d) to carpet the surface of a vessel with a prosthesis, as a "sheathing",
 e) to return a dilated artery (aneurysm) to its normal caliber, or
 f) to isolate the inner surface of an artery from the blood chemical or physical elements, such as, for example, after performing dilatation with a balloon (internal bypass).

Endovascular expanders, commonly known as "stents", are often used to carry out the above techniques. Stents are tubular, permeable, elastic structures that are typically structured in special metallic meshes forming skeletal expandable tubes able to generate radial forces to keep vessels open.

Essentially, there are three general types of expanders or endovascular stents: thermosensitive stents, which adopt predetermined shapes at different temperatures, particularly that of the human body (such as, for example, as described in U.S. Pat. No. 4,425,908); stents expandable with a balloon (such as, for example, as described in European Patent EP 378.151), and stents that are self-expandable through structural elasticity (such as, for example, as described in U.S. Pat. No. 4,580,568 to Cesare Gianturco).

Self-expandable stents are typically compressed inside introductory devices or sheaths. Once the vascular area is reached, the sheath is removed, leaving the expander located endoluminally. Commonly used stents of this type are described in patents to Cesare Gianturco or assigned to Schneider (USA) Inc. of Plymouth, Minn. or Schneider (Europe) A.G. of Bulach, Switzerland.

Because of their structure, self-expanding stents typically experience longitudinal lengthening when compressed inside the sheath. When liberated inside the vascular lumen, they radially expand and longitudinally reduce. This change in shape poses a serious problem when the stent is combined with a Dacron or a polytetraethylene expandable prosthesis that covers the outside of the stent.

When the stent is deployed and expansion occurs, the length of the prosthesis remains essentially unchanged, while the stent noticeably shortens. For example, referring now to FIGS. 1 and 2, there are shown a compressed stent 12 and compressed prosthesis 13 in FIG. 1 and an expanded stent 12' and expanded prosthesis 13' in FIG. 2. FIGS. 1 and 2 illustrate the relatively substantial change in length of stent 12 upon expansion as compared to the insubstantial change in length of prosthesis 13.

Thus, a prosthesis that is the same length as the stent inside the sheath is too long when the stent is liberated. On the contrary, if the prosthesis is too much shorter than the stent inside the sheath, parts of the stent remain without prosthetic cover when the stent opens. Because of the different expansion properties between the prosthesis and the stent, and the frictional relationship between the two in the sheath, irregular expansion of the prosthesis may occur, provoking folds on the prosthesis that act as constrictor rings to limit the expansion of the expander.

Thus there is a need in the art for a deployment device that eliminates such problems associated with concurrent deployment of a stent and prosthesis.

BRIEF SUMMARY OF THE INVENTION

The present invention provides a device for endoluminally placing an endovascular tubular prosthesis in a vascular duct along a guide wire, the prosthesis having flexible walls and a furthest end. The device comprises an introducer exterior sheath and an interior sheath therein, each sheath having valvular means. The prosthesis is positioned between the interior and exterior sheaths, and an elastic expander is compressed inside the interior sheath. The expander has a nearest end and a furthest end that is exteriorly projected to the interior sheath and adapted to be joined to the tubular prosthesis furthest end. A pusher is linked to the expander nearest end.

The pusher may contain a radiopaque substance where it connects to the expander nearest end. The expander may have an expanded length, corresponding to the intraprosthetic position into which it radially expands, that is longer than the length of the prosthesis.

It is to be understood that both the foregoing general description and the following detailed description are exemplary, but are not restrictive, of the invention.

DESCRIPTION OF THE SEVERAL VIEWS OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

The same reference numbers in the Figures indicate equal or corresponding parts. It should be understood that this drawing represents one of its best ways of execution, but only as an illustrative example, without limitation thereto.

DETAILED DESCRIPTION OF INVENTION

Figure 3A:
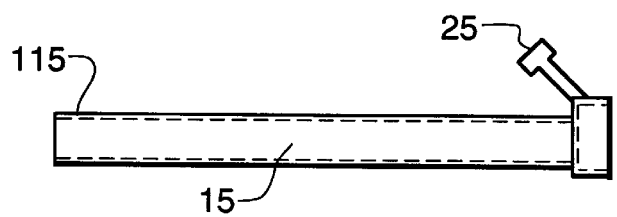
FIG. 3A is a schematic illustration of a lateral view of an interior sheath of a device of the present invention.
Figure 3B:
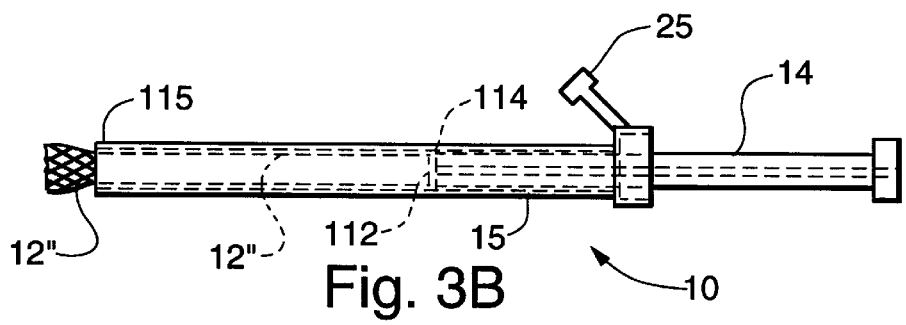
FIG. 3B is a schematic illustration of a lateral view of the interior sheath showing the furthest end of the expander protruding therefrom, and showing with dotted lines the interior arrangement of the pusher and the compressed elastic expander.
Figure 3C:
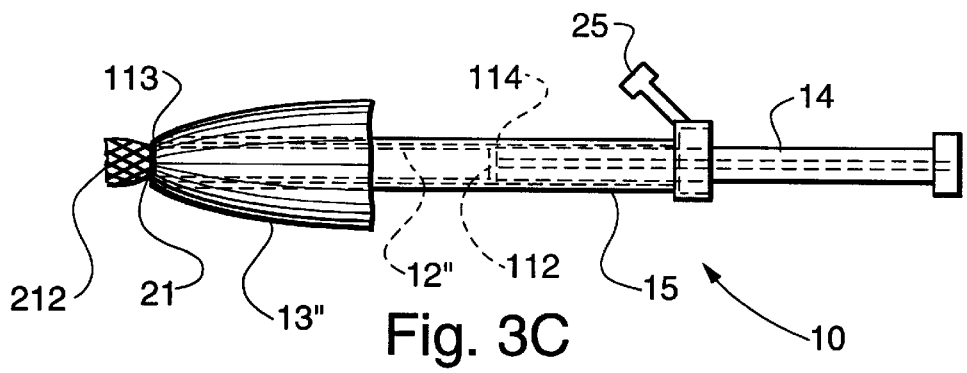
FIG. 3C is a schematic illustration of a lateral view of the interior sheath of FIG. 3B, showing the tubular prosthesis and elastic expander linked by their respective furthest ends.
Figure 3D:
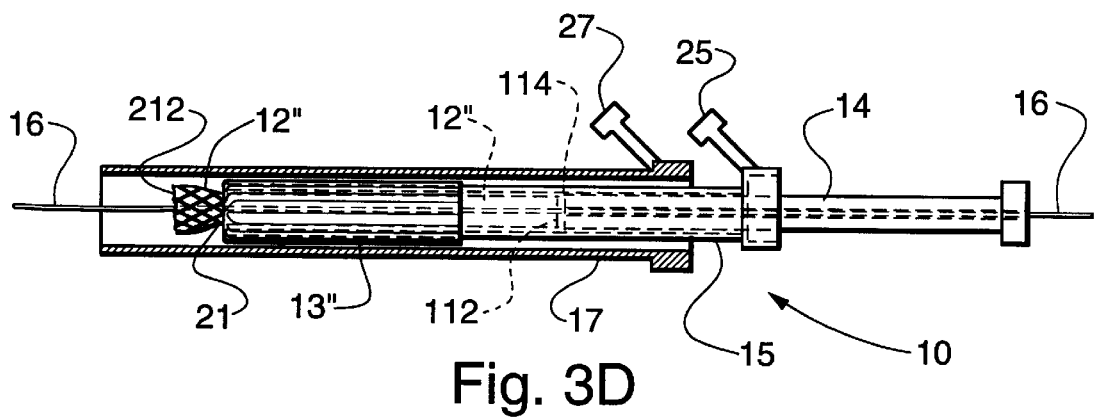
FIG. 3D is a schematic illustration of a lateral view of the device of the present invention, showing the arrangement of the compressed interior sheath and shrunken tubular prosthesis of FIG. 3C inside the exterior sheath.
Figure 4A:
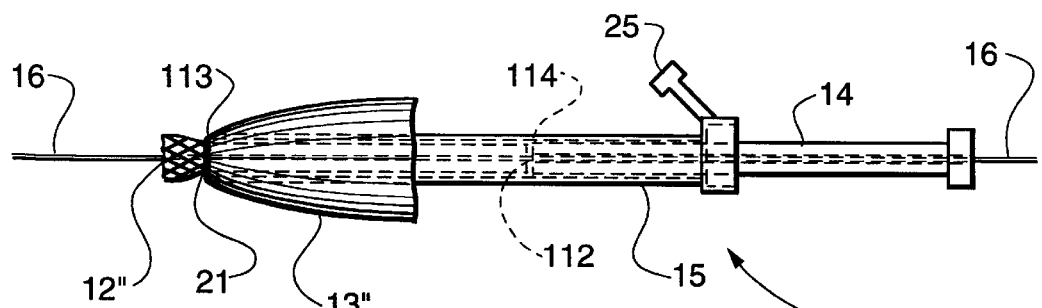
FIG. 4A is a schematic illustration of a lateral view of the interior sheath and attached components of FIG. 3B mounted on the guiding rope.
Figure 4B:
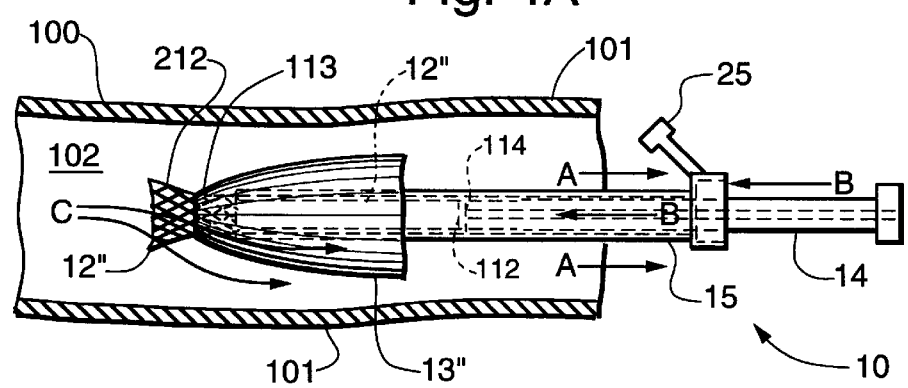
FIG. 4B is a schematic illustration of a lateral view of the device of FIG. 4A within a longitudinal cut of a vascular duct.
Figure 4C:
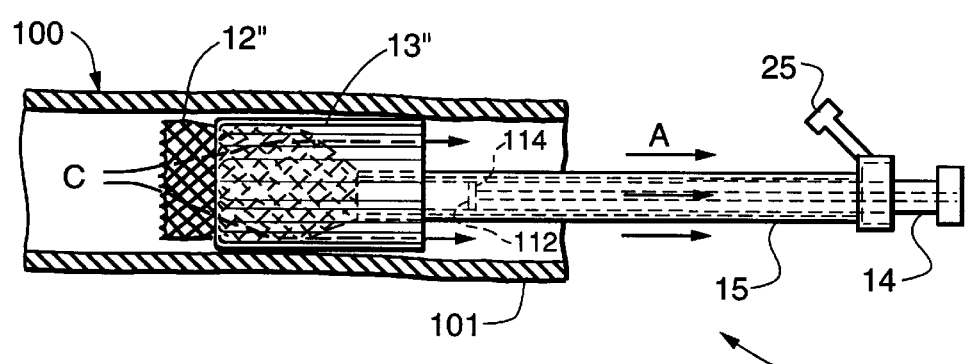
FIG. 4C is a schematic illustration of a lateral view of the device of FIG. 4B showing partial deployment of the expander and prosthesis.
Figure 4D:
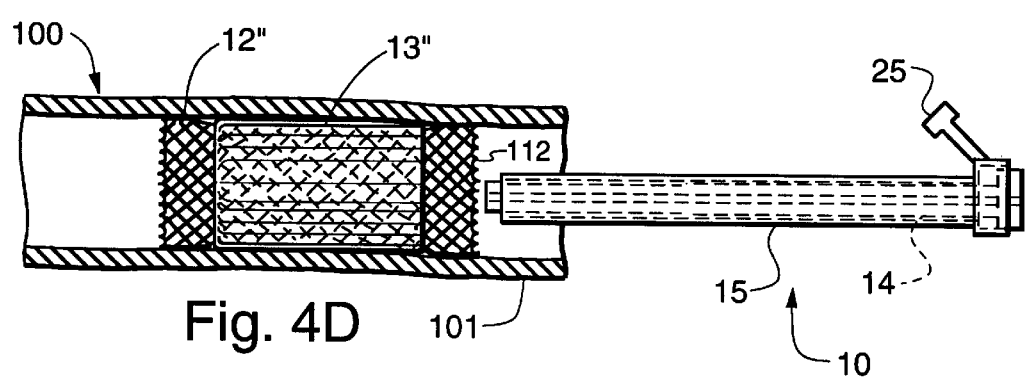
FIG. 4D is a schematic illustration of a lateral view of the device of FIG. 4C showing completed deployment of the expander and prosthesis with retraction of the pusher and interior sheath.

Referring now to the drawing, wherein like reference numerals refer to like elements throughout, FIGS. 3A–4D show an exemplary device 10 for placing an endovascular stent 12" concurrently with an endovascular prosthesis 13". Device 10 is endoluminally introducible inside vascular duct 100, as shown in FIGS. 4B–4D, by s means of a guiding wire 16, as shown in FIGS. 3D and 4A. As shown in FIG. 3D, device 10 comprises an introducer exterior sheath 17 inside of which an interior sheath 15 is placed, inside of which elastic expander 12" is compressed. The nearest end 112 of expander 12" is linked to a pusher 14, and its furthest end 212 is exteriorly projected from the interior sheath 15 and is joined to furthest end 113 of a tubular prosthesis 13". The remaining prosthesis 13" is placed between both sheaths 15 and 17, each of which have respective valvular means 25 and 27.

Figure 1:
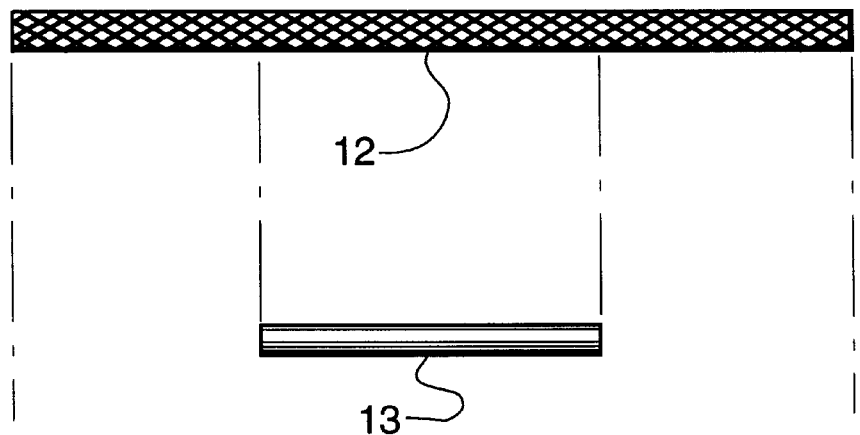
FIG. 1 is a schematic illustration of a lateral view of an elastic expander and tubular prosthesis in their respective radially-expanded positions.

Endovascular prosthesis 13" is tubular with flexible walls, and is inserted into device 10 in a shrunken state similar to that of prosthesis 13' as shown in FIG. 1. Elastic expander 12" is placed inside sheath 15 aligned with tubular prosthesis 13" on the outside of the sheath, with expander furthest end 212 having a link 21 to the corresponding prosthesis furthest end 113, as shown in FIGS. 3C–4C.

Elastic expander 12" is placed so that it is compressed within the tubular interior sheath 15. Elastic expander 12" has its nearest end 112 connected to pusher 14, as shown in FIGS. 3B–4C. Pusher 14 has a connection end 114 that comprises a chuck provided with a radiopaque substance.

Furthest end 212 of elastic expander 12" is exteriorly projected through the outlet end 115 of interior sheath 15. In that exterior projection, link 21 on furthest end 212 of expander 12" is attached to corresponding furthest end 113 of tubular prosthesis 13", as shown in FIGS. 3C–4B.

Tubular prosthesis 13" is partially expanded from a completely compressed state similar to that shown for prosthesis 13 of FIG. 1, so that it covers outlet end 115 of interior sheath 15, in which the compressed elastic expander 12" is placed, as shown in FIGS. 3C.

The components of device 10 as shown in FIG. 3C are placed inside exterior sheath 17 which covers tubular prosthesis 13", such that the prosthesis is placed between the exterior sheath 17 and the interior sheath 15, as shown in FIG. 3D.

Figure 2:
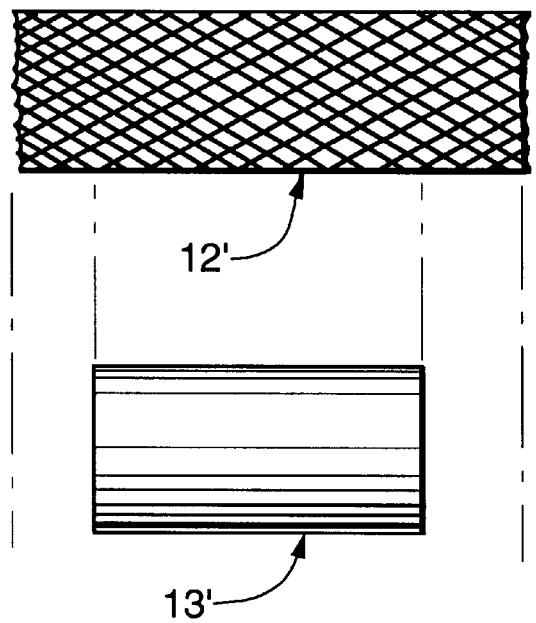
FIG. 2 is a schematic illustration of a lateral view of the elastic expander and tubular prosthesis of FIG. 1 in their compressed and shrunken positions.

As discussed in the background section of this application, prosthesis 13" has flexible walls that can expand without experiencing a noticeable change in length. On the other hand, when compressed elastic expander 12 is liberated from sheath 15, it experiences a radial expansion together with a longitudinal reduction, as shown in FIGS. 1 and 2. Because expander 12" behaves as a radial support of prosthesis 13", the tubular body of prosthesis 13" has a shorter length than the length of expander 12" when it is in a radially expanded state in the desired intraprosthetic position, as shown in FIG. 4D.

To concurrently place expander 12" and prosthesis 13" using device 10, a guiding wire 16 is put into position in vascular duct 100, as is well known in the art. Device 10 is then threaded along guiding wire 16, as shown in FIG. 4A until it reaches a desired position. Once at this position, exterior sheath 17 is retracted in the direction of arrows A while the pusher advances relative to the sheath in the direction of arrows B, leaving the partially compressed tubular prosthesis 13" exposed inside vascular duct 100 in a desired location, as shown in FIG. 4B.

Interior sheath 15 is gradually removed, liberating elastic expander 12", which expands radially. This gradual expansion causes a correlative expansion of the flexible walls of tubular prosthesis 13" until it is pressed against vascular walls 101. At the same time, a radiopaque substance at end 114 of pusher 14 allows movement of the expander 12" to be monitored and thus controlled. While the aforesaid operations are carried out, the device still allows the flow of blood 102 along arrows "C", as shown in FIGS. 4B and 4C.

Although illustrated and described herein with reference to certain specific embodiments, the present invention is nevertheless not intended to be limited to the details shown. Rather, various modifications may be made in the details within the and range of equivalents of the claims and without departing from the spirit of the invention.

I claim:

1. A device adapted to endoluminally place an endovascular tubular prosthesis inside a vascular duct via a guiding wire, the prosthesis having flexible walls and a furthest end, the device comprising:

an introducer exterior sheath and an interior sheath therein, said prosthesis positioned between said sheaths;

an elastic expander compressed inside said interior sheath, said expander having a nearest end and a furthest end, said expander furthest end exteriorly projected from said interior sheath and joined to said tubular prosthesis furthest end.

2. The device according to claim 1, wherein the expander nearest end links to a connection end of a pusher.

3. The device according to claim 2, wherein the connection end contains a radiopaque substance.

4. The device according to claim 1 wherein the prosthesis has a length and the expander has an expanded length corresponding to an intraprosthetic position into which the expander is adapted to radially expand, said expanded length being longer than the prosthesis length.

5. The device according to claim 2 wherein the prosthesis has a length and the expander has an expanded length corresponding to an intraprosthetic position into which the expander is adapted to radially expand, said expanded length being longer than the prosthesis length.

6. The device according to claim 3 wherein the prosthesis has a length and the expander has an expanded length corresponding to an intraprosthetic position into which the expander is adapted to radially expand, said expanded length being longer than the prosthesis length.

* * * * *